(12) United States Patent
Densford

(10) Patent No.: US 8,771,340 B2
(45) Date of Patent: Jul. 8, 2014

(54) METHODS AND DEVICES FOR THE ENDOLUMINAL DEPLOYMENT AND SECUREMENT OF PROSTHESES

(75) Inventor: Eric D. Densford, West Memphis, AR (US)

(73) Assignee: Cook Medical Technologies LLC, Bloomington, IN (US)

( * ) Notice: Subject to any disclaimer, the term of this patent is extended or adjusted under 35 U.S.C. 154(b) by 1732 days.

(21) Appl. No.: 11/510,321

(22) Filed: Aug. 25, 2006

(65) Prior Publication Data

US 2007/0050012 A1 Mar. 1, 2007

Related U.S. Application Data

(60) Provisional application No. 60/711,223, filed on Aug. 25, 2005.

(51) Int. Cl.
*A61F 2/06* (2013.01)

(52) U.S. Cl.
USPC ....... 623/1.24; 623/1.14; 623/1.32; 623/1.36; 623/2.38; 606/200

(58) Field of Classification Search
USPC ................... 623/1.14, 1.24, 1.32, 1.36, 2.38; 606/200
See application file for complete search history.

(56) References Cited

U.S. PATENT DOCUMENTS

| | | |
|---|---|---|
| 4,218,782 A | 8/1980 | Rygg |
| 4,675,361 A | 6/1987 | Ward |
| 4,861,830 A | 8/1989 | Ward |
| 4,902,508 A | 2/1990 | Badylak et al. |
| 4,956,178 A | 9/1990 | Badylak et al. |
| 5,156,620 A | 10/1992 | Pigott |
| 5,156,911 A | 10/1992 | Stewart |
| 5,281,422 A | 1/1994 | Badylak et al. |
| 5,387,450 A | 2/1995 | Stewart |
| 5,411,552 A | 5/1995 | Andersen et al. |
| 5,412,035 A | 5/1995 | Schmitt et al. |
| 5,554,389 A | 9/1996 | Badylak et al. |
| 5,607,465 A | 3/1997 | Camilli |
| 5,855,601 A | 1/1999 | Chuter et al. |
| 5,955,110 A | 9/1999 | Patel et al. |
| 5,993,844 A | 11/1999 | Abraham et al. |
| 6,099,567 A | 8/2000 | Badylak et al. |
| 6,110,201 A | 8/2000 | Quijano et al. |
| 6,126,686 A | 10/2000 | Badylak et al. |
| 6,168,614 B1 | 1/2001 | Andersen et al. |

(Continued)

FOREIGN PATENT DOCUMENTS

| | | |
|---|---|---|
| WO | WO 01/19285 | 3/2001 |
| WO | WO 03/070124 | 8/2003 |
| WO | WO 2004/089253 | 10/2004 |

OTHER PUBLICATIONS

U.S. Appl. No. 60/711,223, filed Aug. 25, 2005, Densford.

*Primary Examiner* — Victor Nguyen
*Assistant Examiner* — Kevin Everage
(74) *Attorney, Agent, or Firm* — Woodard, Edward, Moriarty, McNett & Henry LLP

(57) ABSTRACT

Provided are methods, devices, and systems that can be used to deploy prosthetic devices within a bodily lumen of a patient. These methods and devices can include the securement of a prosthetic valve within a vascular lumen by driving one or more fasteners from a position on an expandable device through the valve and into or through a vascular wall.

62 Claims, 6 Drawing Sheets

(56) References Cited

U.S. PATENT DOCUMENTS

| | | |
|---|---|---|
| 6,200,336 B1 | 3/2001 | Pavcnik et al. |
| 6,206,931 B1 | 3/2001 | Cook et al. |
| 6,245,076 B1 | 6/2001 | Yan |
| 6,287,334 B1 | 9/2001 | Moll et al. |
| 6,299,637 B1 | 10/2001 | Shaolian et al. |
| 6,475,232 B1 * | 11/2002 | Babbs et al. ............. 623/1.13 |
| 6,508,833 B2 | 1/2003 | Pavcnik et al. |
| 6,582,462 B1 | 6/2003 | Andersen et al. |
| 6,620,191 B1 | 9/2003 | Svensson |
| 6,635,078 B1 | 10/2003 | Zhong et al. |
| 6,716,241 B2 | 4/2004 | Wilder et al. |
| 6,752,828 B2 * | 6/2004 | Thornton ................. 623/1.24 |
| 7,871,434 B2 * | 1/2011 | Case et al. ............... 623/2.12 |
| 2001/0011187 A1 | 8/2001 | Pavcnik et al. |
| 2001/0039450 A1 | 11/2001 | Pavcnik et al. |
| 2002/0065552 A1 | 5/2002 | Jayaraman et al. |
| 2002/0123800 A1 | 9/2002 | Taheri et al. |
| 2002/0188348 A1 | 12/2002 | DiMatteo et al. |
| 2003/0036795 A1 | 2/2003 | Andersen et al. |
| 2003/0130726 A1 | 7/2003 | Thorpe |
| 2003/0191525 A1 | 10/2003 | Thornton |
| 2003/0208261 A1 | 11/2003 | Thorpe et al. |
| 2004/0015230 A1 | 1/2004 | Moll et al. |
| 2004/0049262 A1 | 3/2004 | Obermiller et al. |
| 2004/0098098 A1 * | 5/2004 | McGuckin et al. .......... 623/1.14 |
| 2004/0186558 A1 | 9/2004 | Pavcnik et al. |
| 2004/0193253 A1 | 9/2004 | Thorpe et al. |
| 2004/0225322 A1 * | 11/2004 | Garrison et al. ............. 606/200 |
| 2005/0033398 A1 * | 2/2005 | Seguin ..................... 623/1.11 |
| 2007/0027518 A1 * | 2/2007 | Case et al. ................. 623/1.1 |

* cited by examiner

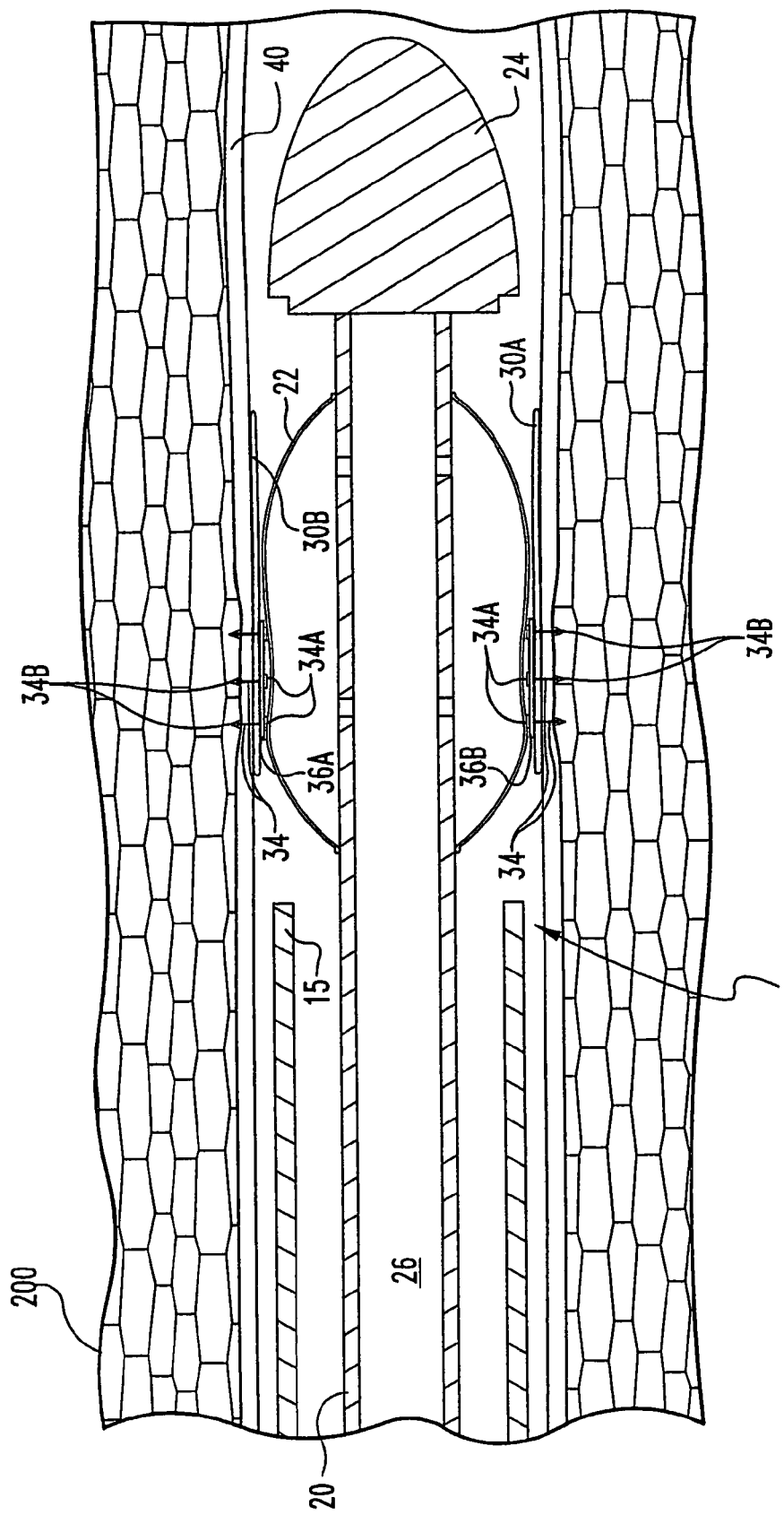

METHODS AND DEVICES FOR THE ENDOLUMINAL DEPLOYMENT AND SECUREMENT OF PROSTHESES

STATEMENT OF RELATED APPLICATIONS

This application claims the benefit of priority of U.S. Provisional Patent Application Ser. No. 60/711,223 filed Aug. 25, 2005. which is incorporated herein by reference in its entirety.

BACKGROUND

The present invention resides generally in the field of devices and methods useful for the deployment of prosthetic devices, and in a particular aspect relates to the deployment of prosthetic devices within the vasculature of a patient to treat complications, such as a varicose vein condition, resultant of venous reflux.

As further background, vascular vessels are comprised of tissue and are the conduit for circulating blood through a mammalian body. A vascular vessel that carries blood from the heart is known as an artery. A vascular vessel that returns blood to the heart is known as a vein. There are three types of veins in a human: deep veins, which are located deep in the body close to the bones, superficial veins, which are located close to the skin, and perforating veins, which are smaller veins that connect the deep veins to the superficial veins.

To assist blood flow, venous vascular vessels contain venous valves. Each venous valve is located inside the vein and typically includes at least two valve leaflets, which are disposed annularly along the inside wall of the vein. These leaflets open to permit blood flow toward the heart and close, upon a change in pressure, such as a transition from systole to diastole, to restrict the back flow of blood. When blood flows towards the heart, the venous pressure forces the valve leaflets to move apart in a downstream flexing motion, thereby creating an open path for blood flow. The leaflets normally flex together when moving in the upstream direction; therefore, they return to a closed position to restrict or prevent blood flow in the upstream, or retrograde, direction after the venous pressure is relieved. The leaflets, when functioning properly, extend radially inward toward one another such that the leaflet tips, or cusps contact each other when the valve is closed.

On occasion, and for a variety of reasons, such as congenital valve or vein weakness, disease in the vein, obesity, pregnancy, and/or an occupation requiring long periods of standing, one or more valves in a vein will allow deleterious retrograde flow to occur. When a valve allows such retrograde flow, blood will collect, or pool in vessels beneath the valve. This pooling of blood causes an increase in the venous pressure below the valve. Venous valves that allow such deleterious retrograde flow are known as incompetent or inadequate venous valves. The condition resulting from such incompetent venous valves is known as venous valve insufficiency.

In the condition of venous valve insufficiency, the venous valve leaflets do not function properly. Incompetent venous valves can cause the veins to bulge, can cause swelling in the patient's lower extremities, and can result in varicose veins and/or chronic venous insufficiency. If left untreated, venous valve insufficiency can cause venous stasis ulcers of the skin and subcutaneous tissue.

A common method of treatment for venous valve insufficiency is the placement of an elastic stocking around the patient's leg to apply external pressure to the vein, forcing the walls radially inward to force the leaflets into apposition. Although sometimes successful, the tight stocking is quite uncomfortable, especially in warm weather, because the stocking must be constantly worn to keep the leaflets in apposition. The elastic stocking also affects the patient's physical appearance, thereby potentially having an adverse psychological affect. This physical and/or psychological discomfort can lead to the patient removing the stocking, thereby inhibiting treatment.

Surgical methods for treatment of venous valve insufficiency have also been developed. A vein with incompetent venous valves can be surgically constricted to bring incompetent leaflets into closer proximity in hopes of restoring natural valve function. Methods for surgical constriction of an incompetent vein include implanting a frame around the outside of the vessel, placing a constricting suture around the vessel (e.g., valvuloplasty), or other types of treatment to the outside of the vessel to induce vessel contraction. Other surgical venous valve insufficiency treatment methods include bypassing or replacing damaged venous valves with autologous sections of veins containing competent valves.

Another surgical method includes vein stripping and ligation. In this procedure, the femoral vein and other major venous tributaries are disconnected from the greater saphenous vein (GSV) and tied off. Next, the GSV is removed from the leg by advancing a wire through the vein, tying the wire to a saphenous vein end, and then pulling the wire, and vein, out through an incision in the upper calf or ankle. Unfortunately, the above surgeries require at least one incision and have several undesirable side effects and risks, such as a long patient recovery time, the potential for scarring, and numerous other risks inherent with surgery, such as those associated with the administration of anesthesia.

Recently, various implantable prosthetic devices and minimally invasive methods for implantation of these devices have been suggested to treat venous valve insufficiency. Such prosthetic devices can be inserted intravascularly, for example from an implantation catheter. Prosthetic devices can function as a replacement venous valve, or enhance venous valve function by bringing incompetent valve leaflets into closer proximity. In one procedure, venous valve function can be enhanced by clipping the valve leaflets together with a clip made from a biocompatible material, such as a metal or polymer. In other procedures, valve leaflets can be attached using a plastic or metal staple or can be fastened with sutures.

Recently, a number of methods have been suggested to treat varicose veins and venous valve leaflets with energy sources, such as radiofrequency (RF) energy. In one such method, valve leaflets can be fastened together with electrodes delivering RF energy. In another such method, a catheter having an electrode tip can be used to apply RF energy to cause localized heating and corresponding shrinkage of venous tissue. After treatment of one venous section is complete, the catheter can be repositioned to treat a different venous section.

Methods for treatment of varicose veins have also been developed involving various forms of sclerotherapy. Generally, sclerotherapy involves the delivery of one or more sclerosing agents to the lumen of a vein, which induce the vein to collapse and the venous walls to fuse, thereby closing the vein.

In view of this background, the need remains for improved and alternative techniques, devices and systems for affecting the venous system to treat venous conditions. The present invention is addressed to these needs.

SUMMARY OF THE INVENTION

Accordingly, in some aspects, the invention provides a medical product for securing a prosthesis within a bodily vessel that includes a number of fasteners arranged over an expandable portion of a delivery device. The delivery device is configured to expand within the vessel to deliver the arranged fasteners into the prosthesis so as to secure the prosthesis within the vessel. The fasteners can have heads that contact the expandable portion of the delivery device, such as by being releasably secured thereto, prior to and during a securement procedure.

In another aspect, the present invention provides a medical product for the securement of one or more prostheses within the vasculature of a patient that includes a percutaneous device having an expandable portion, at least one vascular prosthesis, and one or more fasteners having head portions that contact the expandable portion of the device. The one or more fasteners are configured to secure the at least one vascular prosthesis within patient tissue when the expandable portion of the percutaneous device is expanded within the vasculature of a patient. In certain aspects, the fasteners can be releasably secured to the expandable portion of the percutaneous device.

In yet another aspect, the present invention provides a medical product for securing a prosthesis within a bodily lumen that includes an endoluminal delivery device having an expandable portion and one or more fasteners that are arranged over the expandable portion of the delivery device. The fasteners are configured to be driven into patient tissue by the expansion of the expandable portion of the delivery device so as to secure a prosthesis within a bodily lumen.

In still yet another aspect, the present invention provides a method for implanting prostheses within a bodily lumen of a patient that includes providing a percutaneous device having a surface configured to expand within a bodily lumen of a patient, wherein at least one prosthesis is placed over the expandable surface, and wherein a number of fasteners are located between the expandable surface and a portion of the prosthesis. The method continues by delivering the provided percutaneous device into a bodily lumen of a patient, wherein the expandable surface is positioned at a site within the bodily lumen, and thereafter securing the at least one prosthesis at the site by expanding the surface of the percutaneous device, wherein the one or more fasteners are driven into patient tissue so as to anchor the prosthesis to the patient tissue.

In another aspect, the present invention provides a method for securing a prosthesis within the vasculature of a patient that includes providing a vascular prosthesis and a delivery device that has an expandable segment, wherein one or more fasteners are arranged over the expandable segment of the device. The method continues by locating the provided vascular prosthesis and the provided delivery device at a site within the vasculature of a patient, and thereafter securing the located prosthesis at the vascular site by expanding the expandable segment of the delivery device so as to drive the fasteners into the located prosthesis to anchor the prosthesis at the vascular site.

In yet another aspect, the present invention provides a medical kit that includes sealing an inventive medical product within sterile medical package. In certain aspects, the medical product includes a percutaneous device having an expandable portion, a vascular prosthesis, and one or more fasteners having head portions that contact the expandable portion of the percutaneous device.

The present invention provides improved and/or alternative methods, systems, and devices for deploying and/or securing vascular prostheses within vascular vessels or other prostheses within other bodily vessels. Additional embodiments as well as features and advantages of the invention will be apparent from the further descriptions herein.

BRIEF DESCRIPTION OF THE DRAWINGS

FIG. 3 depicts an illustrative deployment procedure of the present invention.

DETAILED DESCRIPTION

For the purposes of promoting an understanding of the principles of the invention, reference will now be made to certain embodiments thereof and specific language will be used to describe the same. It will nevertheless be understood that no limitation of the scope of the invention is thereby intended, such alterations, further modifications and further applications of the principles of the invention as described herein being contemplated as would normally occur to one skilled in the art to which the invention relates.

As discussed above, certain embodiments of the present invention provide methods, systems, and devices for deploying and/or securing prosthetic devices within vascular vessels in the treatment of certain vascular deficiencies, such as those involved in venous valve insufficiency (VVI). For example, a medical product comprising an arrangement of fasteners located between a prosthetic venous valve and an expandable portion of a percutaneous device can be located within a venous vessel, such as a deep vessel of the lower leg, and the expandable portion of the device can thereafter be expanded so as to deliver the fasteners into patient tissue and deploy the valve within the vein. The deployed valve will be functional to reduce undesirable blood reflux through the lower venous system in the treatment of certain varicosities resulting from VVI. Illustratively, the arranged fasteners can be releasably secured to the percutaneous device to provide for locational stability of the fasteners during placement of the product within the vessel, as well as providing for the removal of the percutaneous device after prosthesis deployment is complete, e.g. by providing for the release of the fasteners from the expandable device, such as during contraction of the expanded device, for example.

Figure 1:
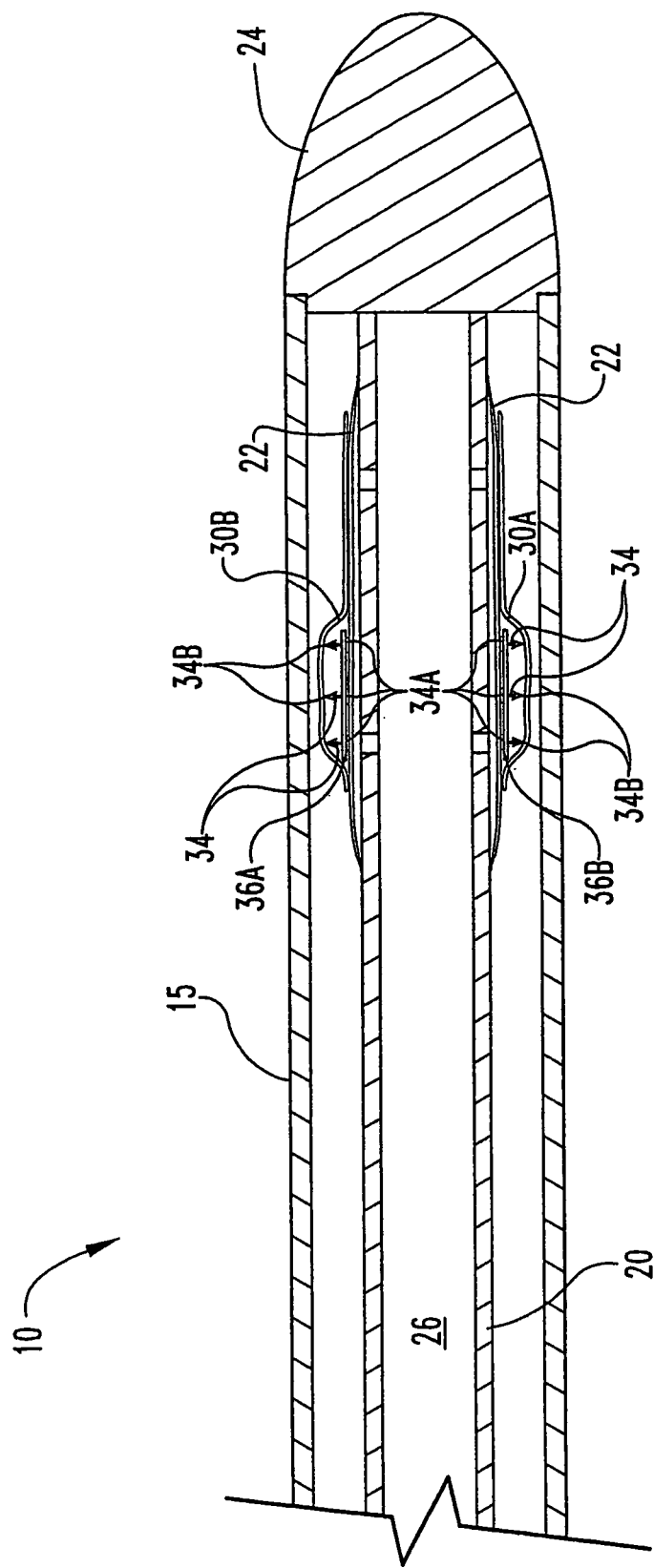
FIG. 1 depicts an illustrative medical device of the present invention.

With reference now to FIG. 1, an illustrative medical product 10 can include a percutaneous delivery device 20 that has an expandable surface or portion 22. The expandable segment 22 can include a balloon which is actuatable by bidirectionally passing a suitable fluid, such as an incompressible fluid, within the lumen 26 of the percutaneous device 20 to either inflate or deflate the balloon 22, as is desirable. The percutaneous device 20 can terminate in a distal tip 24, which can occupy an atraumatic shape that can facilitate placement of the device 20 within a bodily vessel. In certain embodiments, such as where the medical product 10 includes a deployment or delivery sheath 15, the proximal end of the tip 24 can include a lip that is capable of slidably receiving the distal end of the sheath 15.

Referring still to FIG. 1, an illustrative medical product 10 can include one or more fasteners 34 that can be arranged over the expandable segment 22 of the endoluminal device 20. The fasteners 34 can be arranged in a pattern that will impart a suitable anchoring or deployment configuration to a prosthesis, such as a vascular prosthesis 30A, 30B, once the balloon 22 is expanded within a patient and the fasteners are delivered into the prosthesis and patient tissue. In certain embodiments, the vascular prosthesis 30A, 30B can be delivered to a deployment site in tandem with the endoluminal device 20, such as by positioning the prosthesis atop the balloon 22 and fasteners 34, or, alternatively, the prosthesis 30 can be delivered to the deployment site separately from the percutaneous device 20 and fasteners 34, such as in a separate deployment and/or securement procedure wherein the percutaneous device 20 and fasteners 34 are used to further secure and/or enhance the functionality of the separately located prosthesis 30A, 30B.

In illustrative embodiments, each fastener 34 can include a head portion 34A and a tail portion 34B. The tail portion 34B can include a barb that is capable of preventing the fastener 34 from backing out of a pierced portion of the prosthesis 30A, 30B and/or patient tissue. Illustrative such barb configurations can include one or more protuberances that project outwardly at an angle from the tail 34B of the fastener in a downward direction toward the head portion 34A of the fastener 34. As shown in FIGS. 1 through 4B, a number of the arranged fasteners 34 can be connected using any suitable means or technique, as are discussed in more detail below, to form two tack strips 36A, 36B that can be appropriately located over the expandable segment 22 of the percutaneous device 20. The tack strips 36A, 36B can serve to facilitate and maintain the placement of the fasteners 34 in relation to each other, the balloon 22, and/or the prosthesis 30A, 30B during a deployment procedure, for example.

In certain embodiments, such as those depicted in FIGS. 1 through 4B, the tack strips 36A, 36B can be formed by punching the fasteners 34 through two bands of material, such as remodelable material, which is discussed in more detail below. Each band can occupy a shape that corresponds to the desired fastener arrangement. Illustratively, the tack strips 36A, 36B can be positioned on the balloon 22 such that a number of fastener head portions 34A and/or one or more portions of the connecting bands 36A, 36B contact the expandable portion 22 of the percutaneous device 20. If desirable, a number of the fasteners 34 and/or portions or segments of the connecting bands, or tack strips, 36A, 36B can be releasably secured to the balloon 22, using any suitable technique as discussed herein, to enhance the stability of the arranged fasteners during prosthesis 30A, 30B delivery and deployment.

As shown in FIG. 1, an illustrative medical product 10 of the invention can include a vascular device 30A, 30B that is annularly positioned over the endoluminal delivery device 20. The vascular device can include a vascular valve 30A, 30B having two individual valve leaflets that will form a functional valve once each leaflet is fastened within a vascular vessel 40 (see FIGS. 2-4B). As shown, each valve leaflet can be positioned over the arranged fasteners such that a number of fastener tail portions 34B contact one or more portions of each leaflet. If desirable, the valve 30A, 30B leaflets can be attached or connected to a number of the fasteners 34, such as with one or more resorbable sutures or by being at least partially pierced by one or more fastener tail portions 34B.

Turning now to a discussion of certain illustrative deployment methods of the invention, with general reference now to FIGS. 2 through 4B, percutaneous access to a deep vein of the leg 200, such as the femoral vein 40, can be achieved at a suitable access point (not shown) using the Seldinger or any other suitable technique. For instance, an access needle (not shown) can be passed through the skin to access the femoral vein 40, and a wire guide (not shown) can be passed through the access needle and into the vein 40. Prior to the deployment of a prosthetic device, such as a two leaflet venous valve 30A, 30B, the wire guide can be used for any number of conventional procedures including catheterization and imaging procedures in order to locate the deployment site. After any such preliminary procedures that are performed, the wire guide can be used to place an introducer sheath (not shown) at the access point and the wire guide can then be removed. Thereafter, a medical product 10 that includes a deployment sheath 15 containing a vascular valve 30A, 30B and one or more fasteners 34 that overlie an expandable device 22, as discussed above, can be introduced into the femoral vein 40 and the introducer sheath withdrawn, if desirable. The medical product 10 can then be routed through the vein 40, using suitable guidance techniques, e.g. ultrasonic guidance, until the distal end or tip 24 of the product 10 is located near the deployment site.

Figure 2:
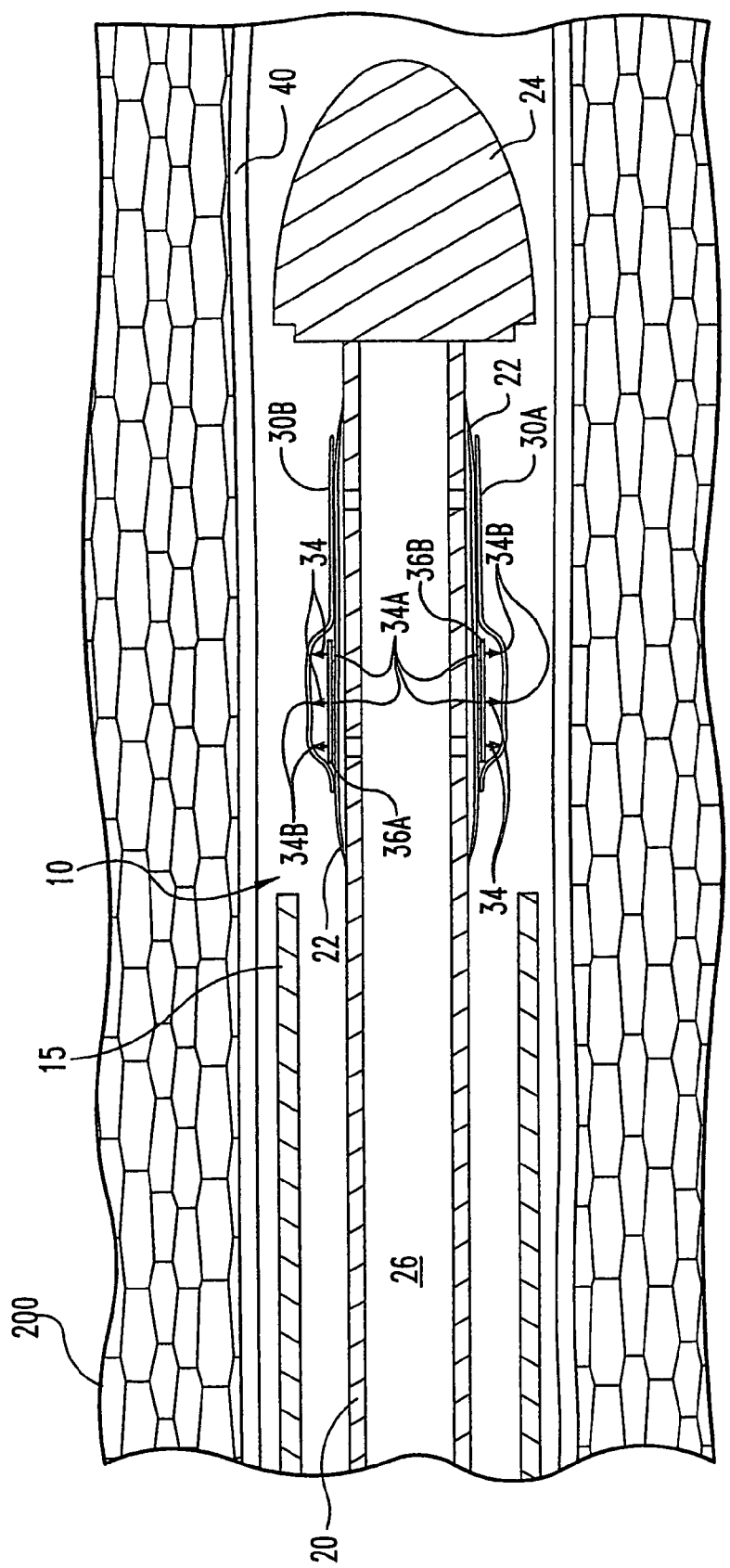
FIG. 2 depicts an illustrative deployment procedure of the present invention.

Turning now more specifically to FIGS. 2 and 3, in certain deployment embodiments, once the venous valve 30A, 30B is positioned near the deployment site, the balloon 22 and the valve 30A, 30B can be exposed within the vein 40 by retracting the sheath 15 in a proximal direction while holding the endoluminal delivery device 20 stationary. Once the valve and balloon are exposed, the endoluminal delivery device 20 can be positioned within the vein 40 until the valve is at the desired deployment site. Thereafter, as is illustratively shown in FIG. 3, the balloon 22 can be expanded within the vein 40 thereby driving the fasteners 34 through the venous valve and into or through the venous wall so as to anchor each valve leaflet 30A, 30B within the vein 40. After the fasteners 34 are delivered and the valve leaflets are secured, the balloon 22 can be deflated and the percutaneous delivery device 20 and the sheath 15 can be retracted from the vein 40.

In certain illustrative embodiments, the tacks are associated with yet not permanently secured or attached to the implant and are driven into the venous wall through a portion of the implant to secure the fasteners and implant together and thereby stabilize the implant within the vessel.

Figure 4A:
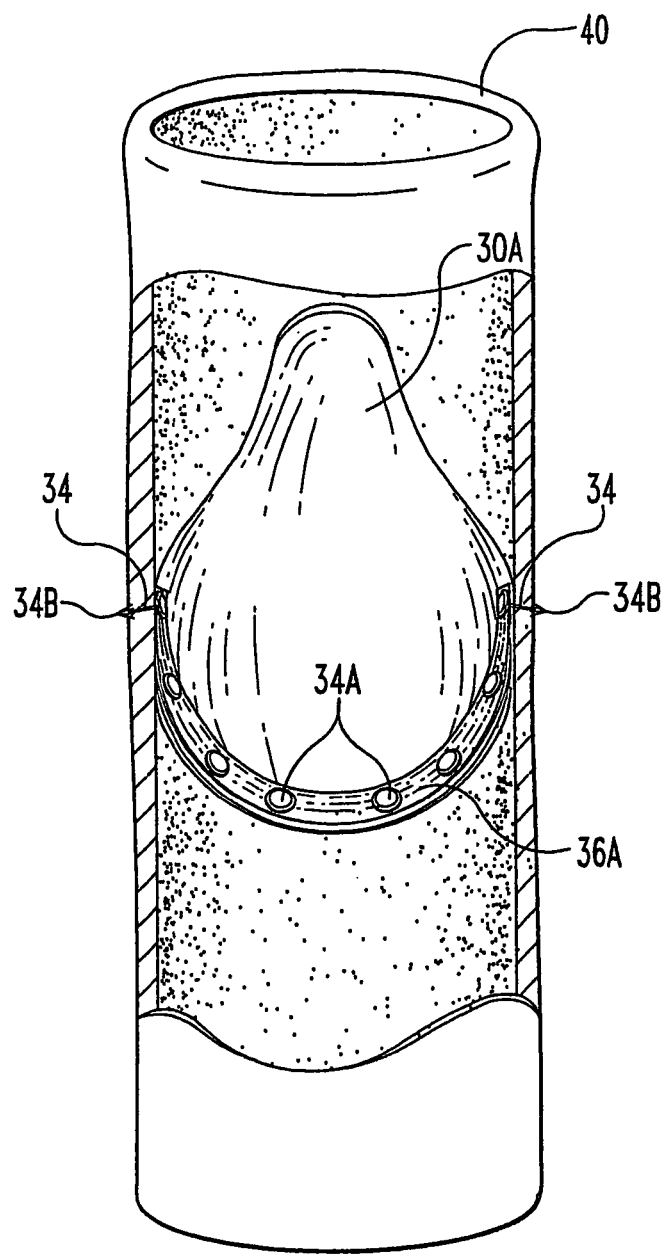
FIG. 4A depicts an illustrative deployment procedure of the present invention.
Figure 4B:
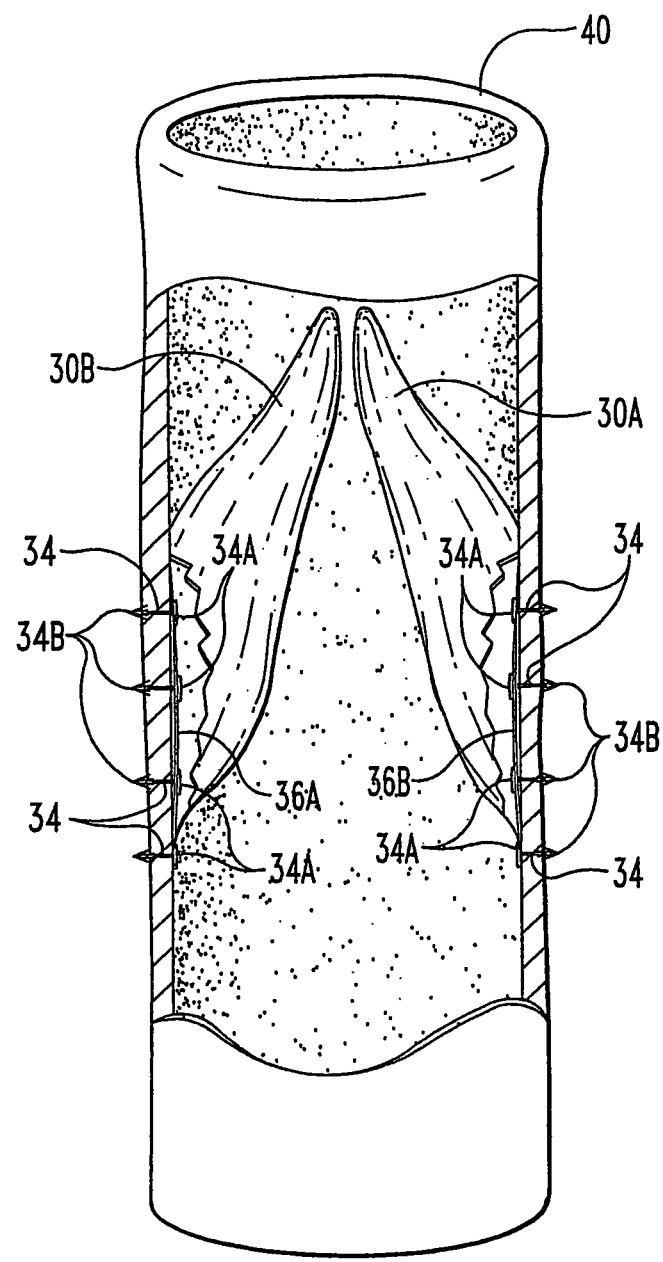
FIG. 4B depicts an illustrative deployment procedure of the present invention.

With reference now to FIGS. 4A and 4B, certain partial venous 40 cross-sections are presented which depict an illustrative functional venous valve 30A, 30B that can be implanted using illustrative devices 10 and procedures of the invention. As shown in FIG. 4A, each valve leaflet 30A, 30B can be secured within the vein 40 using eight fasteners 34 that can be secured together using a suitable band 36A, 36B of material. Each band 36A, 36B extends along a curvilinear path and can serve to maintain the arrangement of the fasteners 34 with respect to each valve leaflet 30A, 30B and can also serve as a bolster material to facilitate the retention of the fasteners 34, such as the fastener heads 34A, within the valve leaflets 30A, 30B. As shown in FIG. 4B, each fastener 34 can have a barbed tail 34B that can penetrate the vessel wall and that can serve to inhibit or prevent the release of the fasteners 34 from the venous wall. Additionally, FIG. 4B depicts the coaptation of each deployed valve leaflet 30A, 30B that will make the valve properly function within the vein 40.

Figure 5:
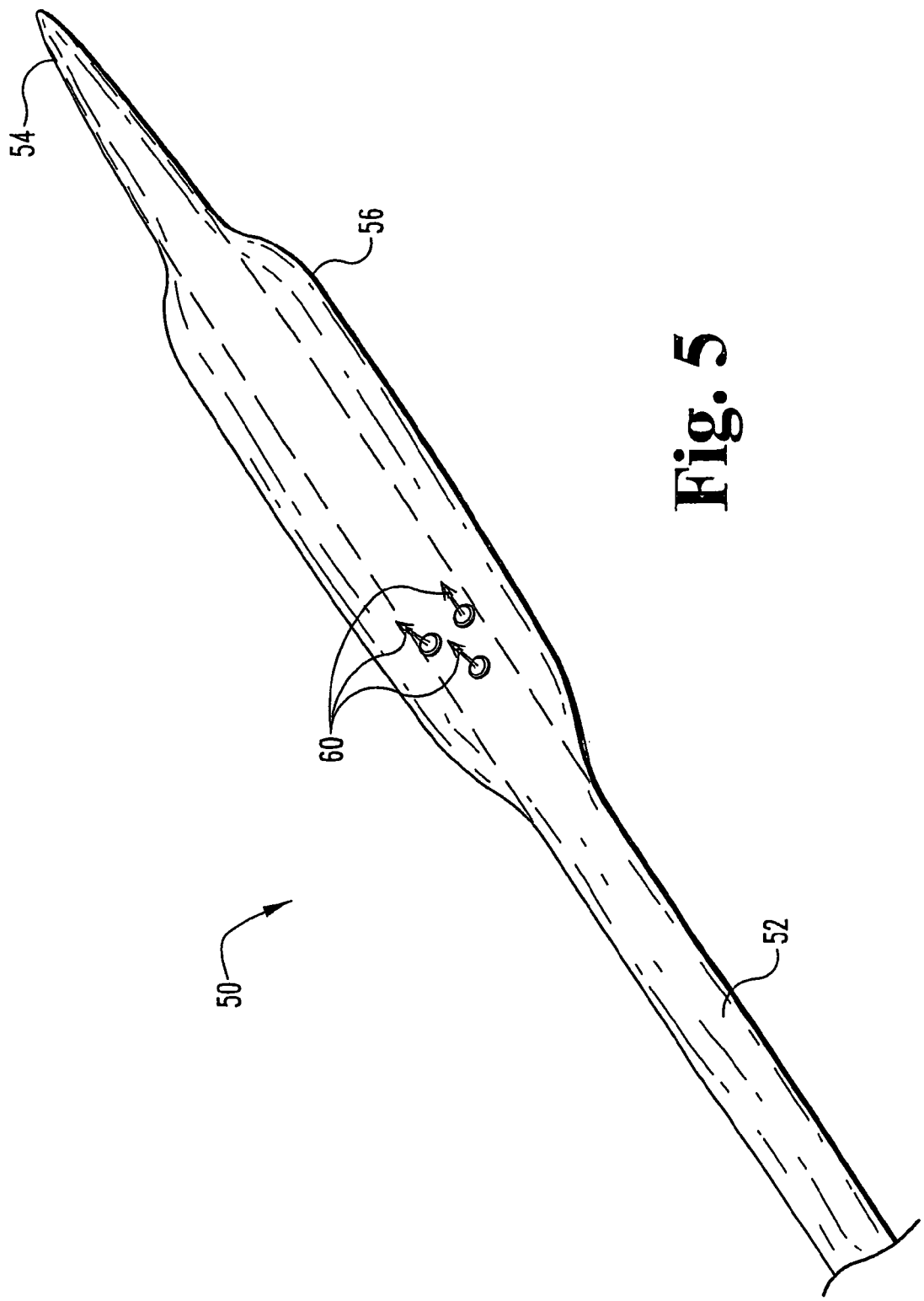
FIG. 5 depicts an illustrative medical device of the present invention.

Turning now to FIG. 5, an illustrative medical product 50 is depicted that can include an endoluminal delivery device 52 that has an atraumatic tip 54 for facilitating the passage if the device 52 through a bodily lumen. Additionally, the medical product 50 can include a number of fasteners 60 that can be positioned over an expandable portion 56 of the percutaneous device 52, such as by being temporarily secured or releasably arranged upon the expandable segment 56, using, for example, a pressure or temperature sensitive adhesive, as are discussed herein.

In illustrative procedures, the medical product 50 can be used to secure an implant within a patient and/or impart certain desirable functionality to an implant. For example, in certain embodiments, the medical product 50 can be used to implant a prosthesis within the patient, such as by delivering the implant to a bodily site in tandem with the percutaneous device and fasteners, for example. In alternative embodiments, the medical product 50 can be used to secure or enhance the functionality of a previously located or previously implanted prosthesis, such as by delivering one or more fasteners to an implanted prosthesis that is in need of repair or securement.

Turning now to a discussion of percutaneous devices that can be useful in certain embodiments of the invention, such percutaneous devices can include any suitable endoluminal device that includes a portion that is capable of expanding within a bodily lumen of a patient to deliver one or more fasteners into patient tissue. Illustrative such devices can include balloon catheters, as are within the purview of one skilled in the art, as well as percutaneous devices having expanding wire arrangements, e.g. a wire basket, such as are described in U.S. Pat. App. Pub. No. 2004/0225322.

Turning now to a discussion of fasteners that can be useful in certain embodiments of the invention, such fasteners can include any securement device having suitable size and shape and can be made from any suitable biocompatible material, as is desirable. Illustrative such sizes and shapes are described herein and are also within the purview of one skilled in the art. Illustrative such biocompatible materials are also within the purview of one skilled in the art and can include metals and metal alloys, such as shape memory alloys, synthetic materials, e.g. Nylon or Teflon, and/or any suitable resorbable or remodelable material, as are discussed below. For more information concerning fasteners and fastener materials that can be useful in certain embodiments of the invention, reference can be made, for example, to International Patent Application Publication No. WO2004/089253.

Turning now to a discussion of suitable devices and methods for connecting one or more fasteners together, such connecting devices can include the use of one or more separate or connected wires, sutures, or bands of material. In certain embodiments, the connecting material may be rigid or semi-rigid so as to maintain a specific desirable fastener arrangement. Illustrative such wires and sutures can be formed from shape memory material, such as nitinol or the like and/or other metallic materials or alloys (stainless steel) and/or resorbable or remodelable materials, as are discussed below, such as a resorbable suture coated with a biodegradable stiffener, such as wax. Illustrative material bands or wires can also include any suitable material, such as a remodelable or resorbable material, a fabric, e.g. Dacron, polymer, e.g. polyvinyl alcohol, or metallic material, that can be formed into a geometric shape that when connected to or through the fasteners will result in the desired arrangement of fasteners being driven into patient tissue. In certain embodiments, the fasteners can be attached to the connecting devices using any suitable technique, depending on the composition of the fasteners and the connector. Illustrative such attaching can be achieved by piercing the connector with the fasteners, wrapping a connector, such as a wire connector, around the fasteners, affixing the connector to the fasteners, such as with sutures for example, or bonding the connector to the fasteners using a suitable adhesive, e.g. a heat or pressure sensitive adhesive (see below) or bonding technique, e.g. soldering.

Turning now to a discussion of materials or devices that can be used to releasably attach the fasteners or a connector onto an expandable segment of a percutaneous device and/or attach the fasteners onto the connector, such materials or devices can include any suitable adhesive, temporary bonding agent, and/or any suitable releasable mechanism or device. Illustrative such temporary bonding agents can include any tacky material that is capable of holding the fasteners and connector material in place during delivery and deployment, yet is capable of releasing the fasteners and connector material, if desirable, upon a change in pressure, temperature, and/or force. A change in pressure can be caused by the contraction or deflation of the expandable segment and/or the longitudinal movement of the percutaneous device and/or by injecting a suitable fluid, e.g. saline, at the deployment site. A change in temperature can be caused by allowing the adhesive to rise to a patient's body temperature, and/or by injecting a temperature controlled fluid, such as saline, at the deployment site. Suitable quantities of such adhesives can be coated onto the expandable portion of the balloon or connector using various methods, such as brushing, wiping, spraying, dipping, or otherwise, either during manufacture of the device or just prior to an illustrative deployment procedure. For more information that can be useful in certain embodiments of the present invention concerning temperature and pressure sensitive adhesives, reference can be made, for example to U.S. Pat. Nos. 5,156,911, 5,387,450, 5,412,035, 6,245,076, 6,635,078. and/or 6,620,191. Illustrative such releasable devices can include a temporary mechanical locking device that can be released, e.g. upon expansion, twisting, or other manipulation of the delivery device, to provide for the delivery and deployment of the fasteners and/or connecting material within a patient.

Turning now to a discussion of prosthetic devices that can be used in certain embodiments of the present invention, suitable prosthetic devices can include any percutaneously deployable device, such as one or more prosthetic valves and/or vascular occlusion devices. For more information on suitable prosthetic valve devices that can be useful in certain embodiments of the present invention, reference can be made, for example to U.S. Pat/App. Nos. 2004/0186558, 6,752,828. and/or International Publication No. WO 2004/089253. filed on Apr. 1, 2004 as PCT/US2004/09971. published on Oct. 21, 2004 and/or U.S. Utility Application titled "Implantable Frame with Variable Compliance," filed on Apr. 11, 2005.

Turning now to a discussion of materials that can be used to form medical devices that can be useful in certain embodiments of the present invention, in certain embodiments, stent frames and anchoring devices, such as barbs or fasteners can include nonresorbable synthetic biocompatible polymers, such as cellulose acetate, cellulose nitrate, silicone, polyethylene teraphthalate, polyurethane, polyamide, polyester, polyorthoester, polyanhydride, polyether sulfone, polycarbonate, polypropylene, high molecular weight polyethylene, polytetrafluoroethylene, or mixtures or copolymers thereof. Illustrative resorbable synthetic materials can include polylactic acid, polyglycolic acid or copolymers thereof, a polyanhydride, polycaprolactone, polyhydroxy-butyrate valerate, polyhydroxyalkanoate, or another biodegradable polymer or mixture thereof. Illustrative metals and metal alloys can include nitinol or other shape-memory materials, or stainless steel. For further information concerning suitable materials (biodegradable, nonbiodegradable, and metallic), useful in certain embodiments of the present invention, reference can be made, for example, to U.S. Utility Patent Application titled, "Implantable Frame with Variable Compliance," filed on Apr. 11, 2005 ("Express Mail" Mailing Label No. EV 327 135 804 US), which claims priority to U.S. Provisional Patent Application Ser. No. 60/561,739 entitled, "Implantable Frame with Variable Compliance," filed on Apr. 13, 2004.

Turning now to a discussion of materials that can be used to form valve leaflets or other stent covering material and/or occlusive prosthetic devices that can be useful in certain embodiments of the present invention, such materials can include any suitable biocompatible material. Generally, such materials may include a remodelable material, such as a resorbable synthetic material, e.g. polyvinyl alcohol foam, or a naturally derived resorbable or remodelable material. Additionally, such materials can include any other suitable naturally derived or any other suitable nonresorbable synthetic material, such as a thromboresistant biocompatible material, e.g. Thoralon® as discussed below, or any combination of any of the above such biocompatible materials. Such biocompatible materials that are at least bioresorbable will provide advantage in certain embodiments of the invention, with materials that are bioremodelable or otherwise tissue inductive so as to promote cellular invasion and ingrowth providing particular advantage.

Illustratively, a thromboresistant biocompatible material can be selected from a variety of materials, but preferably comprises a biocompatible polyurethane material. One particularly preferred biocompatible polyurethane is THORALON (THORATEC, Pleasanton, Calif.), described in U.S. Pat. App. Pub. No. 2002/0065552 and U.S. Pat. No. 4,675,361. both of which are incorporated herein by reference. The biocompatible polyurethane material sold under the tradename THORALON is a polyurethane base polymer (referred to as BPS-215) blended with a siloxane containing surface modifying additive (referred to as SMA-300). The concentration of the surface modifying additive may be in the range of 0.5% to 5% by weight of the base polymer.

THORALON can be used in certain vascular applications and is characterized by thromboresistance, high tensile strength, low water absorption, low critical surface tension, and good flex life. THORALON is biostable and can be useful in vivo in long term blood contacting applications requiring biostability and leak resistance. Because of its flexibility, THORALON is useful in larger vessels, such as the abdominal aorta and other large venous vessels, where elasticity and compliance are beneficial.

The SMA-300 component (THORATEC) is a polyurethane comprising polydimethylsiloxane as a soft segment and the reaction product of diphenylmethane diisocyanate (MDI) and 1,4-butanediol as a hard segment. A process for synthesizing SMA-300 is described, for example, in U.S. Pat. Nos. 4,861,830 and 4,675,361. which are incorporated herein by reference.

The BPS-215 component (THORATEC) is a segmented polyetherurethane urea containing a soft segment and a hard segment. The soft segment is made of polytetramethylene oxide (PTMO), and the hard segment is made from the reaction of 4,4'-diphenylmethane diisocyanate (MDI) and ethylene diamine (ED).

THORALON can be formed as a non-porous material or as a porous material with varying degrees and sizes of pores, as described below. Implantable medical devices can comprise one or both forms of THORALON. The thromboresistant material preferably comprises the non-porous form of THORALON. The porous forms of THORALON can also be used as a thromboresistant material, but are preferably employed as an adhesion promoting region.

Suitable remodelable materials can include collagenous extracellular matrix (ECM) materials, such as submucosa, renal capsule membrane, dura mater, pericardium, serosa, peritoneum, or basement membrane. Preferred remodelable material will include submucosa, such as submucosa derived from a warm-blooded vertebrate. Mammalian submucosa materials are preferred. In particular, submucosa materials derived from animals raised for meat or other product production, e.g. pigs, cattle or sheep, will be advantageous. Porcine submucosa provides a particularly preferred material for use in certain embodiments of the present invention, especially porcine small intestine submucosa (SIS), more especially porcine small intestine submucosa retaining substantially its native cross-linking.

The submucosa or other ECM material can be derived from any suitable organ or other biological structure, including for example submucosa derived from the alimentary, respiratory, intestinal, urinary or genital tracts of warm-blooded vertebrates. Submucosa useful in aspects of the present invention can be obtained by harvesting such tissue sources and delaminating the submucosa from smooth muscle layers, mucosal layers, and/or other layers occurring in the tissue source. For additional information concerning submucosa useful in certain embodiments of the present invention, and its isolation and treatment, reference can be made, for example, to U.S. Pat. Nos. 4,902,508, 5,554,389, 5,993,844, 6,206,931. and 6,099,567.

As prepared and used, the submucosa material or any other ECM material may optionally retain growth factors or other bioactive components native to the source tissue. For example, the submucosa or other ECM material may retain one or more growth factors such as basic fibroblast growth factor (FGF-2), transforming growth factor beta (TGF-beta), epidermal growth factor (EGF), and/or platelet derived growth factor (PDGF). As well, submucosa or other ECM material used in certain embodiments of the invention may retain other biological materials such as heparin, heparin sulfate, hyaluronic acid, fibronectin and the like. Thus, generally speaking, the submucosa or other ECM material may retain a bioactive component that induces, directly or indirectly, a cellular response such as a change in cell morphology, proliferation, growth, protein or gene expression. In certain preferred embodiments of the invention, the ECM material will exhibit the capacity to promote angiogenesis.

Further, in addition or as an alternative to the inclusion of such native bioactive components, non-native bioactive components such as those synthetically produced by recombinant technology or other methods, may be incorporated into the submucosa or other ECM material. These non-native bioactive components may be naturally-derived or recombinantly produced proteins that correspond to those natively occurring in the ECM material, but perhaps of a different species (e.g. human proteins applied to collagenous ECMs from other animals, such as pigs). The non-native bioactive components may also be drug substances or therapeutic agents. Illustrative drug substances that may be incorporated into and/or onto the ECM material can include, for example, antibiotics and/or thrombus-promoting substances such as blood clotting factors, e.g. thrombin, fibrinogen, and the like. These substances may be applied to the ECM material as a premanufactured step, immediately prior to application (e.g. by soaking the material in a solution containing a suitable antibiotic such as cefazolin), or during or after application of the ECM material to the patient.

Submucosa or other ECM material used in certain embodiments of the invention is preferably highly purified, for example, as described in U.S. Pat. No. 6,206,931 to Cook et al. Thus, preferred ECM material will exhibit an endotoxin level of less than about 12 endotoxin units (EU) per gram, more preferably less than about 5 EU per gram, and most preferably less than about 1 EU per gram. As additional preferences, the submucosa or other ECM material may have a bioburden of less than about 1 colony forming units (CFU) per gram, more preferably less than about 0.5 CFU per gram. Fungus levels are desirably similarly low, for example less than about 1 CFU per gram, more preferably less than about 0.5 CFU per gram. Nucleic acid levels are preferably less than about 5 µg/mg, more preferably less than about 2 µg/mg, and virus levels are preferably less than about 50 plaque forming units (PFU) per gram, more preferably less than about 5 PFU per gram. The ECM material useful in certain embodiments of the invention is preferably disinfected with an oxidizing agent, particularly a peracid, such as peracetic acid. These and additional properties of submucosa or other ECM materials taught in U.S. Pat. No. 6,206,931 may be characteristic of the submucosa useful in certain embodiments of the present invention.

Turning now to a discussion of materials useful in certain embodiments of the present invention, sheaths, dilators, wire guides and needles used in the present invention can all be conventional marketed products or modifications thereof. For example, sheaths can be formed from PTFE (e.g. Teflon) or polyamide (e.g. Nylon) material, or a combination of materials such as an assembly including an inner layer of PTFE, a flat wire coil over the PTFE for kink resistance, and a polyamide (Nylon) outer layer to provide integrity to the overall structure and a smooth surface (e.g. as in the Flexor sheath, Cook, Inc.). Dilators can be made from conventional dilator/catheter type materials such as polyethylene, polyamide, polyurethane or vinyl, or any combination of these materials. Fittings provided for sheath/dilator assemblies can be conventional elements such as luer locks, and the dilator can have a fitting allowing it to be locked to the sheath during insertion and manipulation. Catheters can be made from conventional materials such as polyethylene, polyamide, PTFE, polyurethane, and other materials.

As is conventional, the distal ends of the catheters, sheaths, dilators, wires or other components used in percutaneous procedures can include markers that can be X-ray, sonographically, or otherwise non-invasively visualized to identify their location during the procedure. Metallic bands of stainless steel, tantalum, platinum, gold, or other suitable materials, which include a dimple pattern, can serve the purpose for both ultrasound and X-ray identification.

Certain embodiments of the invention can also include medical kits, such as an illustrative medical product that includes one or more fasteners temporarily secured over the deflated balloon of a balloon catheter sealed within sterile medical packaging. The final, packaged product is provided in a sterile condition. This may be achieved, for example, by gamma, e-beam or other irradiation techniques, ethylene oxide gas, or any other suitable sterilization technique, and the materials and other properties of the medical packaging will be selected accordingly. The device may be packaged wet or after it is dried.

All publications cited herein are hereby incorporated by reference in their entirety as if each had been individually incorporated by reference and fully set forth.

While the invention has been illustrated and described in detail in the drawings and foregoing description, the same is to be considered as illustrative and not restrictive in character, it being understood that only the preferred embodiments have been shown and described and that all changes and modifications that come within the spirit of the invention are desired to be protected.

What is claimed is:

1. A medical product for the securement of one or more valve prostheses within the vasculature of a patient, comprising:
    a percutaneous device having an expandable portion configured to expand within the vasculature of a patient;
    at least one vascular valve prosthesis positioned over the expandable portion, the at least one valve prosthesis including at least a first flexible leaflet having a bottom edge region for securement against a wall of a vessel of the vasculature in a first curved path extending partially circumferentially around and longitudinally along the wall of the vessel to form a curved bottom edge of a deployed leaflet configuration within the vessel;
    a first band of bolster material layered on and in contact with the bottom edge region of the first flexible leaflet between the bottom edge region of the first flexible leaflet and the expandable portion;
    the first band of bolster material having first and second ends and a first edge extending therebetween along a curvilinear path when the expandable portion is expanded within the vasculature of a patient so as to track the curved bottom edge of the deployed leaflet; and
    a first plurality of fasteners having a head portion and a body portion, wherein the fasteners are positioned such that the head portion contacts the expandable portion between the first band of bolster material and the expandable portion and wherein the fasteners are configured to extend through both the first band of bolster material and the first flexible leaflet to secure the first band of bolster material and the bottom edge region of the first flexible leaflet to the wall of the vessel in the first curved path extending partially circumferentially around and longitudinally along the wall of the vessel to form the curved bottom edge of the deployed leaflet configuration when the expandable portion is expanded within the vasculature of a patient;
    wherein at least two of the fasteners are connected; and
    wherein the at least two connected fasteners and band of bolster material together comprise a tack strip.

2. The medical product of claim 1, further comprising:
    a sheath having a lumen, a distal end, and a proximal end, wherein the percutaneous device, the at least one vascular prosthesis, and the one or more fasteners are slidably received within the lumen of the sheath.

3. The medical product of claim 2, wherein the percutaneous device terminates in a tip that extends beyond the distal end of the sheath.

4. The medical product of claim 1, wherein the body portion of the fasteners penetrates through the vascular valve prosthesis.

5. The medical product of claim 4, wherein the head portion of each fastener is releasably secured to the expandable portion of the endoluminal delivery device.

6. The medical product of claim 5, wherein the fasteners are releasably secured to the expandable portion of the percutaneous device using an adhesive.

7. The medical product of claim 6, wherein the adhesive comprises a pressure sensitive adhesive, a heat activated adhesive, or any suitable combination thereof.

8. The medical product of claim 1, wherein the at least one vascular valve prosthesis also comprises:
    a second flexible leaflet having a bottom edge region for securement against a wall of a vessel of the vasculature in a second curved path extending partially circumferentially around and longitudinally along the wall of the vessel to form a curved bottom edge of a deployed leaflet configuration for the second flexible leaflet within the vessel;
    a second band of bolster material layered on and in contact with the bottom edge region of the second flexible leaflet between the bottom edge region of the second flexible leaflet and the expandable portion;

the second band of bolster material having first and second ends and a first edge extending therebetween along a curvilinear path when the expandable portion is expanded within the vasculature of a patient so as to track the curved bottom edge of the deployed second flexible leaflet; and a second plurality of fasteners having a head portion and a body portion and positioned such that the head portion contacts the expandable portion between the second band of bolster material and the expandable portion and wherein the fasteners of the second plurality of fasteners are configured to extend through both the second band of bolster material and the second flexible leaflet to secure the second band of bolster material and the bottom edge region of the second flexible leaflet to the wall of the vessel in the second curved path extending partially circumferentially around and longitudinally along the wall of the vessel to form the curved bottom edge of the deployed leaflet configuration for the second flexible leaflet when the expandable portion is expanded within the vasculature.

9. The medical product of claim 8, wherein the first and second leaflets comprise a synthetic material or a remodelable material.

10. The medical product of claim 9, wherein the synthetic material comprises a thromboresistant biocompatible polyurethane material.

11. The medical product of claim 9, wherein the remodelable material comprises a resorbable material or an extracellular matrix material.

12. The medical product of claim 11, wherein the extracellular matrix material comprises mammalian porcine submucosa.

13. The medical product of claim 10, wherein the head portion of each fastener is releasably secured to the expandable portion of the endoluminal delivery device.

14. The medical product of claim 13, wherein the fasteners are releasably secured to the expandable portion of the percutaneous device using an adhesive.

15. The medical product of claim 14, wherein the adhesive comprises a pressure sensitive adhesive, a heat activated adhesive, or any suitable combination thereof.

16. The medical product of claim 8, wherein the head portion of each fastener is releasably secured to the expandable portion of the endoluminal delivery device.

17. The medical product of claim 16, wherein the fasteners are releasably secured to the expandable portion of the percutaneous device using an adhesive.

18. The medical product of claim 8, wherein:
the first and second flexible leaflets are independently securable against the wall of the vessel.

19. The medical product of claim 1, wherein the fasteners are arranged in a pattern.

20. The medical product of claim 19, and wherein the tack strip is releasably secured to the expandable portion of the percutaneous device.

21. A medical kit, comprising:
the medical product of claim 1 sealed within sterile medical packaging.

22. The medical product of claim 1, wherein the fasteners extend along the curved path along the bottom edge of the leaflet.

23. The medical product of claim 1, wherein the head portion of each fastener is releasably secured to the expandable portion of the endoluminal delivery device.

24. The medical product of claim 23, wherein the fasteners are releasably secured to the expandable portion of the percutaneous device using an adhesive.

25. The medical product of claim 24, wherein the adhesive comprises a pressure sensitive adhesive, a heat activated adhesive, or any suitable combination thereof.

26. The medical product of claim 1, wherein:
the first band of bolster material has a second edge tracking the curved bottom edge of the deployed leaflet.

27. The medical product of claim 1, wherein:
the first flexible leaflet in the deployed leaflet configuration is secured against the wall of the vessel entirely by the first plurality of fasteners.

28. A medical product for securing a prosthesis within a bodily lumen, comprising:
an endoluminal delivery device having an expandable portion;
an endoluminal valve prosthesis received on the expandable portion, the valve prosthesis including at least a first flexible leaflet having a bottom edge region for securement against a wall of the bodily lumen in a first curved path extending partially circumferentially around and longitudinally along the wall of the bodily lumen to form a curved bottom edge of a deployed leaflet configuration within the bodily lumen;
a first band of bolster material layered on and in contact with the bottom edge region of the first flexible leaflet between the bottom edge region of the first leaflet and the expandable portion;
the first band of bolster material having first and second ends and a first edge extending therebetween along a curvilinear path when the expandable portion is expanded within the vasculature of a patient so as to track the curved bottom edge of the deployed leaflet; and
a first plurality of fasteners that each have a head portion and a body portion, wherein the fasteners are arranged over the expandable portion of the endoluminal delivery device with at least a portion of the endoluminal valve prosthesis overlaying the one or more fasteners and with the head portion of the one or more fasteners contacting the expandable portion of the endoluminal delivery device between the first band of bolster material and the expandable portion, and wherein the fasteners are configured to extend through both the first band of bolster material and the first flexible leaflet and be driven into patient tissue by the expansion of the expandable portion of the endoluminal delivery device so as to secure the first band of bolster material and the bottom edge region of the first leaflet to the wall of the bodily lumen in said curved path extending partially circumferentially around and longitudinally along the wall of the bodily lumen to form the curved bottom edge of the deployed leaflet configuration;
wherein at least two of the fasteners are connected; and
wherein the at least two connected fasteners and band of bolster material together comprise a tack strip.

29. The medical product of claim 28, wherein the head portion of each fastener is temporarily secured to the expandable portion of the endoluminal delivery device.

30. The medical product of claim 29, wherein the fasteners terminate in a barb.

31. The medical product of claim 30, wherein the barb comprises an outwardly projecting protuberance at its tissue piercing end for resisting back out of the barb from patient tissue.

32. The medical product of claim 28, wherein the head portion of the fasteners is positioned on a first side of the endoluminal valve prosthesis, and wherein the body portion of the fasteners extends through the band of bolster material and penetrates through the endoluminal prosthesis and extends outwardly from a second side of the endoluminal prosthesis, said second side opposite said first side.

33. The medical product of claim 32, wherein the head portion of the fasteners is releasably secured to the expandable portion of the delivery device.

34. The medical product of claim 32, wherein the one or more fasteners are releasably secured to the expandable portion of the delivery device using an adhesive.

35. The medical product of claim 34, wherein the adhesive comprises a pressure sensitive adhesive, a heat activated adhesive, or any suitable combination thereof.

36. The medical product of claim 28, wherein the tack strip is releasably secured to the expandable portion of the delivery device.

37. The medical product of claim 36, wherein the band of bolster material comprises a remodelable material.

38. The medical product of claim 37, wherein the remodelable material comprises an extracellular matrix material.

39. The medical product of claim 38, wherein the tack strip is releasably secured to the expandable portion of the delivery device using fibrin glue.

40. The medical product of claim 28, wherein the endoluminal prosthesis also comprises:
a second flexible leaflet having a bottom edge region for securement against the wall of the bodily lumen in a second curved path extending partially circumferentially around and longitudinally along the wall of the bodily lumen to form a curved bottom edge of a deployed leaflet configuration for the second flexible leaflet within the lumen;
a second band of bolster material layered on and in contact with the bottom edge region of the second flexible leaflet between the bottom edge region of the second flexible leaflet and the expandable portion;
the second band of bolster material having first and second ends and a first edge extending therebetween along a curvilinear path when the expandable portion is expanded within the vasculature of a patient so as to track the curved bottom edge of the deployed second flexible leaflet; and
a second plurality of fasteners having a head portion and a body portion and positioned such that the head portion contacts the expandable portion between the second band of bolster material and the expandable portion and wherein the fasteners of the second plurality of fasteners are configured to extend through both the second band of bolster material and the second flexible leaflet and secure the second band of bolster material and the bottom edge region of the second flexible leaflet to the wall of the bodily lumen in the second curved path extending partially circumferentially around and longitudinally along the wall of the bodily lumen to form the curved bottom edge of the deployed leaflet configuration for the second flexible leaflet when the expandable portion is expanded within the bodily lumen.

41. The medical product of claim 40, wherein the first and second bands of bolster material comprise a remodelable material.

42. medical product of claim 41, wherein the remodelable material comprises a resorbable material or an extracellular matrix material.

43. The medical product of claim 42, wherein the extracellular matrix material comprises mammalian porcine submucosa.

44. The medical product of claim 40, wherein the fasteners are releasably secured to the expandable portion of the endoluminal delivery device.

45. The medical product of claim 44, wherein the fasteners are releasably secured to the expandable portion of the percutaneous device using an adhesive.

46. The medical product of claim 45, wherein the adhesive comprises a pressure sensitive adhesive, a heat activated adhesive, or any suitable combination thereof.

47. A method for implanting prostheses within a bodily lumen of a patient, comprising:
providing a percutaneous device having a surface configured to expand within a bodily lumen of a patient, wherein at least one valve prosthesis is placed over the surface, wherein the valve prosthesis includes at least one flexible leaflet having a bottom edge region for securement against a wall of the bodily lumen in a curved path extending partially circumferentially around and longitudinally along the wall of the bodily lumen to form a curved bottom edge of a deployed leaflet configuration within the bodily lumen, further wherein a band of bolster material is layered on and in contact with the bottom edge region of the at least one flexible leaflet between the bottom edge region of the leaflet and the surface configured to expand and has first and second ends and a first edge extending therebetween along a curvilinear path-when the expandable portion is expanded within the vasculature of a patient so as to track the curved bottom edge of the deployed leaflet, and further wherein a plurality of fasteners having a head portion and a body portion are located between the surface and the band of bolster material such that each fastener head contacts the expandable surface of the percutaneous device;
delivering the provided percutaneous device into a bodily lumen of a patient, wherein the surface is positioned at a site within the bodily lumen; and
securing the at least one valve prosthesis at the site by expanding the surface of the percutaneous device, wherein the one or more fasteners are driven into patient tissue so as to extend through both the band of bolster material and the bottom edge region of the leaflet and anchor the band of bolster material and the bottom edge region of the leaflet to the wall of the bodily lumen in said curved path extending partially circumferentially around and longitudinally along the wall of the bodily lumen to form the curved bottom edge of the deployed leaflet configuration;
wherein at least two of the fasteners are connected; and
wherein the at least two connected fasteners and band of bolster material together comprise a tack strip.

48. The method of claim 47, wherein the head portion of each fastener is temporarily secured to the expandable surface of the percutaneous device.

49. The method of claim 48, wherein the fasteners are releasably secured to the expandable portion of the endoluminal delivery device.

50. The method of claim 49, wherein the fasteners are releasably secured to the expandable portion of the percutaneous device using an adhesive.

51. The method of claim 50, wherein the adhesive comprises a pressure sensitive adhesive, a heat activated adhesive, or any suitable combination thereof.

52. The method of claim 47, wherein the at least one valve prosthesis comprises a resorbable material or an extracellular matrix material.

53. The medical product of claim 52, wherein the extracellular matrix material comprises mammalian porcine submucosa.

54. A method for securing a prosthesis within the vasculature of a patient, comprising:
- providing a delivery device having an expandable segment and a plurality of fasteners having a head portion and a body portion, wherein the fasteners are arranged over the expandable segment of the delivery device, wherein with the head portion of the arranged fasteners contacts the expandable segment of the delivery device;
- providing a vascular valve prosthesis that includes at least one flexible leaflet having a bottom edge region for securement against a wall a vessel of the vasculature in a curved path extending partially circumferentially around and longitudinally along the wall of the vessel to form a curved bottom edge of a deployed leaflet configuration within the vessel;
- providing a band of bolster material layered on and in contact with the bottom edge region of the at least one flexible leaflet between the bottom edge region of the leaflet and the expandable segment of the delivery device and has first and second ends and a first edge extending therebetween along a curvilinear path when the expandable portion is expanded within the vasculature of a patient so as to track the curved bottom edge of the deployed leaflet;
- locating the provided vascular prosthesis, the provided band of bolster material, and the provided delivery device at a site within the vasculature of a patient; and
- securing the located band of bolster material and vascular prosthesis at the vascular site by expanding the expandable segment of the delivery device, wherein the fasteners are driven into the band of bolster material, the bottom edge region of the at least one flexible leaflet and the wall of the vessel so as to anchor the leaflet at the vascular site;
- wherein at least two of the fasteners are connected; and
- wherein the at least two connected fasteners and band of bolster material together comprise a tack strip.

55. The method of claim 54, wherein the body portion of the arranged fasteners comprises a barb.

56. The method of claim 55, wherein the head portion of the fasteners is releasably arranged on the expandable segment of the delivery device.

57. The method of claim 56, wherein the fasteners are releasably secured to the expandable portion of the percutaneous device using an adhesive.

58. The method of claim 57, wherein the adhesive comprises a pressure sensitive adhesive, a heat activated adhesive, or any suitable combination thereof.

59. The method of claim 54, wherein the vascular prosthesis and delivery device are located in tandem.

60. The method of claim 54 wherein the vascular prosthesis is delivered to the site separately from the delivery device having fasteners.

61. The method of claim 54, wherein the at least one valve prosthesis comprises a resorbable material or an extracellular matrix material.

62. The medical product of claim 61, wherein the extracellular matrix material comprises mammalian porcine submucosa.

* * * * *